United States Patent [19]

Putter et al.

[11] 4,102,997
[45] Jul. 25, 1978

[54] ACID DEGRADATION PRODUCTS OF BOROMYCIN

[75] Inventors: Irving Putter, Martinsville; Lucille J. Cole, Roselle Park, both of N.J.

[73] Assignee: Merck & Co., Inc., Rahway, N.J.

[21] Appl. No.: 744,020

[22] Filed: Nov. 22, 1976

[51] Int. Cl.$^2$ .............................................. A61K 35/00
[52] U.S. Cl. .................................... 424/115; 424/122
[58] Field of Search ................................. 424/122, 115

[56] References Cited

U.S. PATENT DOCUMENTS

| | | | |
|---|---|---|---|
| 3,769,418 | 10/1973 | Prelog et al. | 424/121 |
| 3,864,479 | 2/1975 | Miller et al. | 424/185 |

OTHER PUBLICATIONS

Putter et al., Helvetica Chimica Acta, vol. 50, 1967, pp. 1533–1538.

*Primary Examiner*—Jerome D. Goldberg
*Attorney, Agent, or Firm*—Walter Patton

[57] ABSTRACT

A novel mixture of degradation products of boromycin is prepared by treating boromycin with acid. This mixture of compounds has anticoccidial activity and is useful for controlling cecal and/or intestinal coccidiosis when administered in minor quantities to animals, in particular to poultry, usually in admixture with animal sustenance.

6 Claims, 1 Drawing Figure

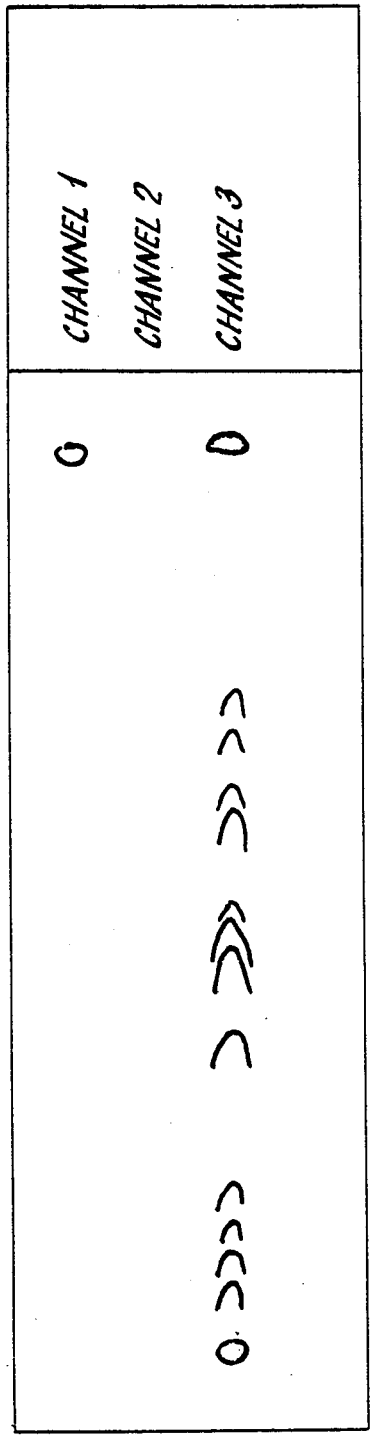

ACID DEGRADATION PRODUCTS OF BOROMYCIN

BACKGROUND OF THE INVENTION

This invention relates to new chemical compounds and the method for preparing the same. It relates further to the use of the new compounds for treating and preventing coccidiosis. This invention still more particularly relates to a novel mixture of degradation products obtained by acid treatment of boromycin and the use of the same in the control and treatment of coccidiosis.

Coccidiosis is a widespread poultry disease which is produced by infections of protozoa of the genus Eimeria which causes severe pathology in the intestines and ceca of poultry. Some of the most significant of these species are *E. tenella, E. acervulina, E. necatrix, E. brunetti* and *E. maxima*. This disease is generally spread by the birds picking up the infectious organism in droppings on contaminated litter or ground, or by way of food or drinking water. The disease is manifested by hemorrhage, accumulation of blood in the ceca, passage of blood in the droppings, weakness and digestive disturbances. The disease often terminates in the death of the animal, but the fowl which survive severe infections have had their market value substantially reduced as a result of the infection. Coccidiosis is, therefore, a disease of great economic importance and extensive work has been done to find new and improved methods for controlling and treating coccidial infections in poultry.

Boromycin is an ionophoric macrolide and methods for obtaining it are disclosed in U.S. Pat. No. 3,769,418, issued Oct. 30, 1973. The use of boromycin as an anticoccidial agent is disclosed in U.S. Pat. No. 3,864,479, issued Feb. 4, 1975.

SUMMARY OF THE INVENTION

This invention is based on the surprising and totally unexpected discovery that treatment of boromycin with acid results in a mixture of degradation products which has a surprisingly and unexpectedly high degree of activity against coccidiosis of poultry. Administering a small amount of this mixture, preferably in combination with poultry feed, is effective in preventing or greatly reducing the incidence of coccidiosis. The mixture is effective against both the cecal form (caused by *E. tenella*) and the intestinal forms (principally caused by *E. acervulina, E. brunetti, E. maxima* and *E. necatrix*). In addition to preventing the pathology caused by coccidia, these compounds also exert an inhibitory effect on the oocysts by greatly reducing the number and/or the sporulation of those produced.

The novel mixture of boromycin degradation products of this invention is prepared from the starting material, boromycin. This starting material is disclosed in U.S. Pat. No. 3,769,418 which is herein incorporated by reference. The novel mixture of compounds of the present invention is prepared by treating boromycin or a salt of boromycin dissolved in a suitable solvent with an excess of acid. The resulting reaction solution is neutralized and the boromycin degradation products separated from inorganic salts.

Any suitable solvent in which boromycin or the salt of boromycin is soluble and to which both are inert, may be used in preparing the degradation products of boromycin. However, the preferred solvents are polar organic solvents such as alcohols or halogenated hydrocarbons. The preferred alcohols are those containing 1 to 6 carbon atoms such as methanol, ethanol, n-propanol and isopropanol. The preferred halogenated hydrocarbons are those such as chloroform, bromoform and methylene chloride. The most preferred solvents are absolute ethanol and chloroform.

The preferred salt of boromycin is an alkali metal salt, selected from any of the univalent basic metals of Group I of the periodic table such as lithium, sodium or potassium. The sodium salt is the preferred salt in the present invention. The salts are prepared by neutralizing boromycin with a weak base such as sodium bicarbonate or potassium bicarbonate or other such weak bases having a monovalent anion to form the sodium, potassium or like salt. The details of salt formation are well known to those skilled in the art.

The acids used for preparing the degradation products of boromycin are selected from any of the following groups: mineral acids, aromatic sulfonic acids, Lewis acids and strongly acidic cation exchange resins. The preferred mineral acids are sulfuric acid, nitric acid and hydrochloric acid. The preferred aromatic sulfonic acids are sulfosalicylic acid and p-toluenesulfonic acid. The preferred Lewis acid is titanium tetrachloride (in chloroform solvent) and the preferred strongly acidic cation exchange resins are the sulfonic acid type having a styrenedivinylbenzene matrix such as Dowex-50, hydrogen form (manufactured by Dow Chemical Co., Midland, Michigan).

In a preferred process for preparing the acid degradation products of boromycin of the present invention one equivalent of boromycin or sodium salt of boromycin is dissolved in ethanol. To this is added an excess of concentrated HCl. The reaction solution is agitated from 2 to 4 hours, preferably at about room temperature. The solution is diluted with water and the pH adjusted to about neutral with inorganic base or neutralized by passage through a column packed with a polystyrene amine anion exchange resin and the eluate concentrated in vacuo to a syrup containing the degradation products. In the case wherein the reaction solution is neutralized with inorganic base, the precipitated salts are removed by centrifugation and the supernatant fluid containing the desired degradation products is decanted and concentrated in vacuo to a syrup.

The concentrates can be incorporated as such into poultry feed to treat coccidiosis or the concentrates can be further purified by chromatography on silica gel.

It is, therefore, a primary object of this invention to provide a novel mixture of acid degradation products of boromycin which mixture is useful in the control of coccidiosis.

Another object of this invention is to provide novel anticoccidial agents.

Still another object of this invention is to provide novel feed compositions useful for the prevention and suppression of coccidiosis in poultry.

A further object of this invention is to provide a new and useful method for the control of coccidiosis in poultry which comprises administering to the poultry minor amounts of the anticoccidial substances of this invention.

A still further object of this invention is to provide a method for preparing a novel mixture of acid degradation products of boromycin.

These and further objects of this invention will become apparent or be described as the description thereof herein proceeds.

DESCRIPTION OF THE PREFERRED EMBODIMENTS

In accordance with this invention, coccidiosis in poultry is controlled or suppressed by administering to the poultry a non-toxic, anticoccidially effective quantity of a mixture of acid degradation products of boromycin.

In preparing the novel coccidiostat of this invention, boromycin on the sodium salt of boromycin is dissolved in absolute ethanol to which is added 10 equivalents of concentrated HCl. The solution is stirred at room temperature for 3 hours and neutralized by passage through a column packed with the polystyrene amine resin, IR-45 in the hydroxide form. The eluate is collected and concentrated in vacuo to a syrup.

Alternatively, the reaction solution is neutralized by the addition of a methanolic solution of KOH. The inorganic salts are removed by centrifugation, and the supernatant liquid containing the boromycin degradation products is concentrated to a syrup.

Thin Layer Chromatography of Boromycin Acid Degradation Products

The mixture of degradation products resulting from the acid treatment of boromycin or a salt of boromycin can be defined by its TLC profile on silica gel plates using the solvent system chloroform:methanol (19:1). The separated components of the degradation mixture, as well as, boromycin, can be visualized with reagents such as iodine, ninhydrin, vanillin-sulfuric acid and water. A diagrammatic representation of a TLC profile for the degradation mixture appears in FIG. 1. With reference to FIG. 1, the thin layer chromatography was run on a E. Merck 60-254F silica gel plate in chloroform:methanol (19:1). The spots were visualized with iodine vapor. With reference to FIG. 1, the Channels 1 to 3 were spotted at the origin with the following components:

Channel 1: boromycin
Channel 2: boromycin and acid degradation products of boromycin
Channel 3: acid degradation products of boromycin.

Column Chromatography of Boromycin Acid Degradation Products

The mixture of degradation products resulting from acid treatment of boromycin or a salt of boromycin can also be defined by its behavior on silica gel column chromatography. For example, 1.09 g. of the degradation mixture in chloroform was charged to a silica gel column (100 ml. bed volume) formed in chloroform. Five fractions were obtained using solvents of increasing polarity to elute the column. The solvents used and the weights of the residues obtained after evaporation of the solvent from each fraction are given below.

| Solvent | Residue Weight (g.) |
| --- | --- |
| Chloroform (250 ml.) | 0.001 |
| 30% Ether in chloroform (400 ml.) | 0.024 |
| Ethyl acetate (400 ml.) | 0.182 |
| Acetone (400 ml.) | 0.760 |
| Methanol (400 ml.) | 0.353* |

*This fraction contained material not soluble in acetone and thus contains material solubilized from the adsorbant by methanol.

It should be noted that none of the fractions from the column chromatography of the degradation mixture showed activity against coccidiosis when assayed at levels corresponding to their actual presence in the mixture. However, when the column fractions were recombined in amounts proportional to their levels in the degradation mixture, the resulting mixture was as active as the unseparated degradation mixture.

The novel compounds of this invention are orally administered to poultry for the control and prevention of coccidiosis. Any number of conventional methods are suitable for administering the coccidiostat of this invention to poultry, as for example, they may be given in the poultry feed or included in drinking water. The actual quantity of the coccidiostat administered to the poultry in accordance with this invention will vary over a wide range and be adjusted to individual needs, depending upon species of the coccidia involved and severity of the infection. The limiting criteria are that the minimum amount is sufficient to control coccidiosis and the maximum amount is such that the coccidiostat does not result in any undesirable effects.

A feed will typically contain from about 0.0005 to about 0.05%, preferably from about 0.0025 to about 0.01% by weight of the coccidiostat of this invention. The optimum levels will naturally vary with the species of Eimeria involved, and can be readily determined by one skilled in the art. Levels of acid degradation products of boromycin of this invention, in poultry feed of from about 0.004% to about 0.008% by weight of the diet are especially useful.

Levels of 0.005% to 0.05% possess the effects of reducing the number of oocysts passed in the droppings of infected chickens and/or inhibiting the subsequent division and maturation to infectivity, scientifically designated as the process of sporulation. Thus, the combination of prevention of pathology, coupled with the inhibiting effects on the reproductive product of these organisms, the oocysts, present a unique two-fold method for the control of coccidiosis in poultry.

The quantity or concentration of the novel coccidiostat of this invention in any admixture in which it is administered to the poultry will, of course, vary in accordance with the type of admixture utilized.

Of the various methods of administering the coccidiostat of this invention to poultry, it is most conveniently administered as a component of a feed composition. The novel coccidiostat may be readily dispersed by mechanically mixing the same in finely ground form with the poultry feedstuff, or with an intermediate formulation (premix) that is subsequently blended with other components to prepare the final poultry feedstuff that is fed to the poultry. Typical components of poultry feedstuffs include molasses, fermentation residues, corn meal, ground and rolled oats, wheat shorts and middlings, alfalfa, clover and meat scraps, together with mineral supplements such as bone meal and calcium carbonate and vitamins.

Suitable compositions also include feed premixes in which the active ingredient is present in relatively large amounts and which are suitable for addition into the feed either directly or after an intermediate dilution or blending step. Such compositions may also be added to the animals feed in the form of a top dressing. Typical carriers or diluents suitable for such compositions include for example, distillers dried grains such as corn distiller's dried grains and corn distiller's grains, corn meal and corn meal germ, citrus meal, fermentation residues, ground oyster shells, wheat shorts and wheat standard middlings, molasses solubles, corncob meal, edible bean mill feed, soyagrits, crushed limestone and the like. The coccidiostat is intimately dispersed throughout the carrier by methods such as grinding, stirring, milling or tumbling. Compositions containing from about 0.1 to 50% by weight, especially from about 0.5 to 25% by weight of the compound are particularly suitable as feed premixes.

Examples of typical feed premixes containing boromycin acid degradation products dispersed in a solid inert carrier are:

|   |   | lbs. |
|---|---|------|
| A. | Boromycin acid degradation products | 6.0 |
|    | Wheat standard middlings | 94.0 |
| B. | Boromycin acid degradation products | 10.0 |
|    | Corn distiller's dried grains | 90.0 |
| C. | Boromycin acid degradation products | 20.0 |
|    | Corn germ meal | 30.0 |
|    | Corn distiller's grains | 50.0 |

The following non-limiting examples will serve to further illustrate the instant invention.

EXAMPLE 1

Preparation of Boromycin Acid Degradation Products

Boromycin, 100 g. (0.113 moles), was dissolved in 200 ml. absolute ethanol. To this solution was added 100 ml. concentrated HCl (1.20 moles, approx. 10 equivalents of boromycin). The solution was stirred at room temperature for 3 hours. The reaction solution was neutralized by passing through a column packed with 2 liters IR-45 in the hydroxide form. The effluent was concentrated in vacuo to a syrup and flushed with ethyl acetate. The final volume of the syrup was 950 ml. containing a total of 103.6 g. boromycin acid degradation products.

EXAMPLE 2

Preparation of Boromycin Acid Degradation Products

Boromycin sodium salt, 250 mg., was dissolved in 25 ml. absolute ethanol. To this solution was added 0.25 ml. concentrated HCl with stirring and the solution agitated for 24 hours.

To the reaction solution was added 2 ml. 1N KOH in methanol with stirring. The reaction mixture was centrifuged to remove the precipitate. The supernatant liquid was decanted and evaporated in vacuo to a syrup. The syrup was taken up in a minimum volume of CHCl$_3$ and applied on a column packed with 75 ml. silica gel in CHCl$_3$. The column was eluted with 300 ml. 5% methanol in CHCl$_3$ followed by 300 ml. 10% methanol in CHCl$_3$. The 5% methanol in CHCl$_3$ eluate was evaporated in vacuo to give 157 mg. of boromycin acid degradation products in the form of a syrup.

EXAMPLE 3

Preparation of Boromycin Acid Degradation Products

Treatment of sodium boromycin (1 equivalent) with the following acids (10 equivalents) in absolute ethanol gave reaction mixtures whose TLC profiles resembled that from the hydrochloric acid treatment. The reaction mixtures showed activity against coccidiosis.

Mineral Acids
    Sulfuric, Nitric, Hydrochloric
Aromatic Sulfonic Acids
    Sulfosalicylic, p-Toluenesulfonic
Lewis Acid
    Titanium tetrachloride (reaction in chloroform)
Strong Cation Exchange Resin
    Dowex-50, hydrogen form Although this invention has been described in relation to specific embodiments, it will be apparent that obvious modifications may be made by one skilled in the art without departing from the intended scope thereof as defined by the appended claims.

What is claimed is:

1. A mixture of boromycin acid degradation products prepared by the process comprising:
(a) treating boromycin or a salt of boromycin dissolved in a suitable solvent with approximately 10 equivalents of acid selected from the group consisting of mineral acids, aromatic sulfonic acids, Lewis acids and strong cation exchange resins for approximately 2 to 4 hours at about room temperature wherein said mineral acids are selected from the group consisting of sulfuric acid, nitric acid and hydrochloric acid; said aromatic sulfonic acids are selected from the group consisting of sulfosalicylic acid and p-toluenesulfonic acid; said Lewis acid is titanium tetrachloride and said strong cation exchange resin is a sulfonic acid resin in the hydrogen form having a styrenedivinylbenzene matrix;
(b) neutralizing the reaction solution by adjusting the pH to about neutral with inorganic base or neutralizing by passage through a column packed with a polystyrene amine anion exchange resin and concentrating the eluate in vacuo to a syrup containing the degradation products; and
(c) in the case wherein the reaction solution is neutralized with inorganic base, removing the precipitated salts by centrifugation and decanting and concentrating the supernatant in vacuo to a syrup.

2. A composition for the treatment of coccidiosis comprising an inert carrier and a coccidiostatically effective amount of a mixture of bromycin acid degradation products as define in claim 1.

3. A composition according to claim 2 wherein said mixture comprises from 0.0005% to 0.05% by weight of said composition.

4. A composition according to claim 3 wherein said mixture comprises from 0.0025% to 0.01% by weight of said composition.

5. A composition according to claim 2 wherein said composition is a feed premix and said mixture comprises from 0.1 to 50% by weight of the premix.

6. A composition according to claim 5 wherein said mixture comprises from 0.5 to 25% by weight of said premix.

* * * * *